(12) United States Patent
Korn

(10) Patent No.: US 6,980,573 B2
(45) Date of Patent: Dec. 27, 2005

(54) TUNABLE SPECTROSCOPIC SOURCE WITH POWER STABILITY AND METHOD OF OPERATION

(75) Inventor: Jeffrey A. Korn, Lexington, MA (US)

(73) Assignee: InfraReDx, Inc., Cambridge, MA (US)

(*) Notice: Subject to any disclaimer, the term of this patent is extended or adjusted under 35 U.S.C. 154(b) by 273 days.

(21) Appl. No.: 10/314,648

(22) Filed: Dec. 9, 2002

(65) Prior Publication Data

US 2004/0109478 A1    Jun. 10, 2004

(51) Int. Cl.[7] .............................................. H01S 3/00
(52) U.S. Cl. ...................................... 372/20; 600/476
(58) Field of Search ...................... 372/29.022, 20–33, 372/8, 109; 600/342, 324–326, 476–478; 606/2, 3, 7, 8, 15; 359/330, 326–332

(56) References Cited

U.S. PATENT DOCUMENTS

| | | | |
|---|---|---|---|
| 5,022,042 A | | 6/1991 | Bradley |
| 5,077,747 A | | 12/1991 | Hemmer et al. |
| 5,263,037 A | * | 11/1993 | Trutna et al. .................. 372/20 |
| 5,318,024 A | * | 6/1994 | Kittrell et al. ............... 600/478 |
| 5,428,635 A | | 6/1995 | Zhiglinsky et al. |
| 5,496,305 A | * | 3/1996 | Kittrell et al. ................. 606/15 |
| 5,785,658 A | * | 7/1998 | Benaron et al. ............. 600/473 |
| 6,055,451 A | * | 4/2000 | Bambot et al. .............. 600/476 |
| 6,081,539 A | | 6/2000 | Mattori et al. |
| 6,088,373 A | | 7/2000 | Hakki |
| 6,095,982 A | * | 8/2000 | Richards-Kortum et al. ..... 600/476 |
| 6,174,291 B1 | * | 1/2001 | McMahon et al. ........... 600/564 |
| 6,564,088 B1 | * | 5/2003 | Soller et al. ................. 600/478 |
| 6,654,630 B2 | * | 11/2003 | Zuluaga et al. .............. 600/476 |
| 6,683,895 B2 | | 1/2004 | Pilgrim et al. |

FOREIGN PATENT DOCUMENTS

| | | |
|---|---|---|
| EP | 0 793 314 A1 | 9/1997 |
| EP | 1 059 712 A2 | 12/2000 |
| EP | 1 168 538 A1 | 1/2002 |
| WO | WO 02/29944 A1 | 4/2002 |

OTHER PUBLICATIONS

Sorin, Wayne V. et al., "Single-frequency Output from a Broadband-tunable External Fiber-cavity Laser," Optics Letters, vol. 13, No. 9, Sep. 1, 1988, pp. 731-733.

Brinkmeyer E., et al., "Fibre Bragg Reflector for Mode Selection and Line-Narrowing of Injection Lasers," Electronics Letters, IEE Stevenage, GB, vol. 22, No. 3, Jan. 30, 1986, pp. 134-135.

* cited by examiner

Primary Examiner—Minsun Oh Harvey
Assistant Examiner—Tuan N. Nguyen
(74) Attorney, Agent, or Firm—Houston Eliseeva LLP

(57) ABSTRACT

A laser system for a spectroscopic catheter system utilizes an overmoded cavity in order to reduce mode hoping induced power fluctuations during wavelength scanning. In the preferred embodiment, a semiconductor gain medium is used to reduce cost. A fiber pigtail is used to define the laser cavity, which has a tight cavity mode spacing of less that 15 Gigahertz. A diffraction grating is used as the tuning element. A cylindrical lens is used to reduce alignment tolerances and thereby increase manufacturability.

22 Claims, 4 Drawing Sheets

TUNABLE SPECTROSCOPIC SOURCE WITH POWER STABILITY AND METHOD OF OPERATION

BACKGROUND OF THE INVENTION

Tunable laser sources are applicable to a number of diagnostic and therapeutic medical applications. Optical coherence tomography is used to provide spatial resolution, enabling the imaging of internal structures. Spectroscopy is used to characterize the composition of structures, enabling the diagnosis of medical conditions, by differentiating between cancerous, dysplastic, and normal cellular structures. Fluorescence and exogenous chromospores can be used to increase the signal to noise ratio in these processes, providing for more accurate diagnostics.

For example, in one configuration for spectroscopy, the tunable laser source is used to scan a spectral band of interest, such as a scan band in the near infrared or 850 nanometers (nm) to 1–2 micrometers ($\mu$m), for example. The generated light is used to illuminate tissue in a target area. Diffusely reflected light resulting from the illumination is then collected and transmitted to a detector. By correlating the scanning of the tunable laser source to the time varying response of the detector, the spectral response of the target area tissue can be resolved. Statistical techniques can be further used to extract useful information from even low-resolution spectral data. For example, chemometrics, which combines spectroscopy and mathematics, can provide clear qualitative as well as quantitative information.

One specific example of an application for spectroscopy concerns the diagnosis of atherosclerosis. This is an arterial disorder involving the intimae of medium- or large-sized arteries, including the aortic, carotid, coronary, and cerebral arteries. Atherosclerotic lesions or plaques contain a complex tissue matrix, including collagen, elastin, proteoglycans, and extracellular and intracellular lipids with foamy macrophages and smooth muscle cells. In addition, inflammatory cellular components (e.g., T lymphocytes, macrophages, and some basophiles) can also be found in these plaques. Efforts are being made to spectroscopically analyze blood vessel walls in vivo using infrared wavelengths to identify and assess the compositions of atherosclerotic lesions.

SUMMARY OF THE INVENTION

The tunable light sources required for these applications ideally have a specific set of operating parameters that distinguish them from functionally similar devices used in other applications. For example, most semiconductor-based lasers naturally have short optical cavities. The laser chips themselves are usually less than 1 millimeter long. Short cavities advantageously, for most applications, result in narrow, spectrally-pure laser signals since only one longitudinal mode oscillates at any moment of operation. In contrast, in spectroscopic applications such as for detection of atherosclerotic lesions, the spectral features of interest are relatively broad. Thus, a narrow linewidth is not a necessity. Moreover, the scan speed must be relatively fast, especially for in vivo measurements, in order to reduce the occurrence of motion induced artifacts.

Another requirement for spectroscopic tunable laser sources is power stability across the scan. The detector reports the level of reflected light in order to resolve the spectrum. The level of reflected light is dependent upon, in part, the level of incident light. Longitudinal mode hopping, however, is a characteristic of lasers, and especially tunable lasers, that can affect instantaneous amount of light generated by the laser as it scans.

A laser operates by the establishment of a standing wave within the optical cavity. In a fixed length cavity, only a discrete set of standing waves can be established. This phenomenon is characterized by the cavity's mode spacing, which is c/(2 L), where c is the speed of light in a vacuum and L is the cavity's optical path length, taking into account the index of refraction. Hopping from one cavity mode to the next causes output power fluctuation because the modes experience slightly different gain in the cavity, which affects the laser's instantaneous output power.

The present invention is directed to a tunable laser source having stable output power during wavelength scanning, and specifically a tunable source that is designed for a spectroscopic catheter system. When compared tunable sources for other applications, the inventive source has an overmoded laser cavity. That is, the longitudinal mode spacing is very close, allowing multiple modes to resonant simultaneously. As a result, as the source tunes over its scan band, changes in how the optical power is distributed in the lasing modes does not lead to any material change in the source output power, because the large number of lasing modes in the cavity's gain bandwidth tends to minimize the impact of changes in power in any individual mode. As a result, output power fluctuations due to mode-hopping are mitigated as the laser is scanned. There will still be power fluctuations from mode-beating, but these are high-frequency.

In general, according to one aspect, the invention features a tunable laser source having stable output power during wavelength scanning. The source comprises a laser cavity that includes a wavelength selector for scanning a passband over a scan band and a laser gain chip, providing gain to longitudinal modes of the laser cavity. The wavelength selector allows net gain to longitudinal modes within a certain gain bandwidth determined by the wavelength selector's passband. According to the invention, the laser cavity is characterized by a cavity longitudinal mode spacing that is more than two times smaller than the gain bandwidth. As a result, multiple longitudinal modes lase simultaneously, thereby improving power stability during scanning.

Exemplary scan bands for the detection of atherosclerotic lesions include 1100 to 1450 nanometers (nm) generally, or 1100 nm to 1350 nm, 1150 nm to 1250 nm, 1175 nm to 1280 nm, and 1190 nm to 1250 nm, more specifically.

In the current embodiment, the wavelength selector comprises a bulk diffraction grating, although acousto-optic filters and Bragg gratings can be used in other configurations.

In the preferred embodiment, the laser cavity further comprises an optical fiber pigtail coupling the laser gain chip and the wavelength selector. This improves manufacturability and also decreases the source's sensitivity to changes in ambient air pressure, such as with altitude.

An output coupler for coupling laser light out of the laser cavity is preferably provided to supply the light to a catheter, which is inserted into a patient.

The laser gain chip preferably comprises a semiconductor optical amplifier, such as a reflective semiconductor optical amplifier.

In order to ensure that multiple longitudinal modes are lasing over the scan, the laser cavity is preferably made long. In the current embodiment, the cavity is greater than 10 centimeters, and preferable greater than 50 centimeters. This yields an overmoded cavity in which the modes have a spacing of less than 15 Gigahertz (GHz), and preferable less than 1.5 GHz. This coupled with a wide gain bandwidth ensures that multiple modes lase simultaneously. Specifically, the gain bandwidth is greater than 10 GHz, and preferably greater than 50 GHz.

Two gain chips can be used to increase power or the spectral width of the scan band. The chip or chips are preferably contained within one or more pigtailed hermetic packages, for ease of manufacturing.

In general, according to another aspect, the invention features a spectroscopic catheter system, which comprises a catheter for insertion into a patient to transmit light to the patient and a tunable laser source. According to the invention, the source has a laser cavity that includes a wavelength selector for scanning a passband over a scan band. A laser gain chip provides gain to modes of the laser cavity within a gain bandwidth provided by the passband. An output coupler couples laser light from laser cavity into the catheter. At least one detector is provided for detecting light returning from the patient. The laser cavity is characterized by a cavity mode spacing that is more than two times smaller than the gain bandwidth.

In the current application, the catheter is inserted into a lumen of the patient such as a blood vessel and advanced to the patient's heart.

In general according to another aspect, the invention can also be characterized as a method for providing tunable frequency light to a patient. The method comprises inserting a catheter into a patient, generating light with a tunable laser, tuning a frequency of the light across a scan band, and detecting light returning from the patient to determine a spectral response of tissue within the patient over the scan band. The length of a laser cavity of the tunable laser is selected so that more than two longitudinal modes of the laser cavity are lasing at all times during the step of tuning the frequency of the light across the scan band.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
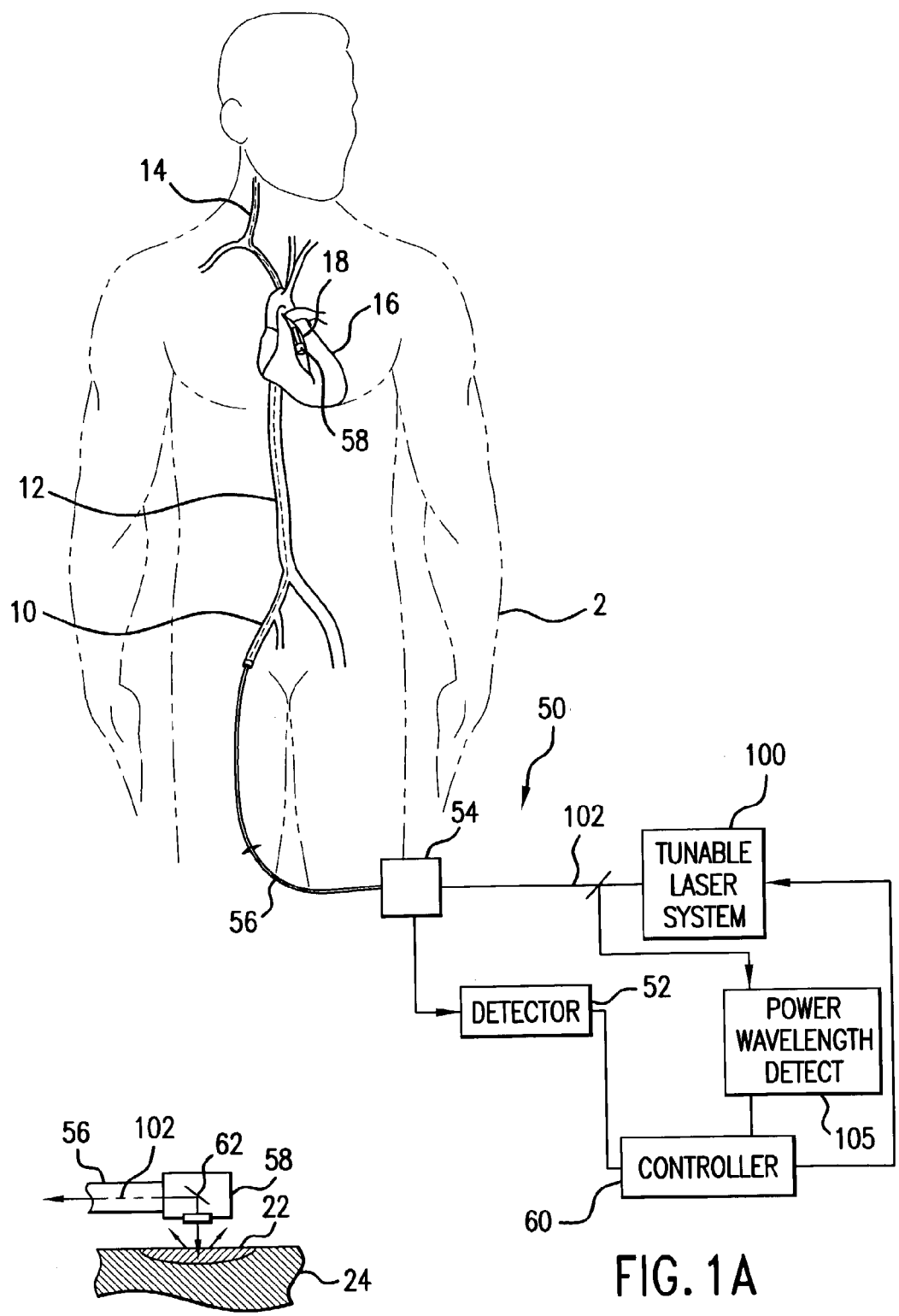
FIG. 1A is a schematic block diagram illustrating the spectroscopic catheter system for the tunable laser source of the present invention.
FIG. 1B is a cross-sectional view of the catheter head positioned for performing spectroscopic analysis on a target region of a blood vessel.

FIG. 1A shows a spectroscopic catheter system 50 to which the tunable laser source 100, of the present invention, is applicable.

Specifically, the catheter system 50 comprises a catheter 56 that includes an optical fiber or optical fiber bundle. The catheter 56 is typically inserted into the patient 2 via a peripheral vessel, such as the femoral artery 10. The catheter head 58 is then moved to a desired target area, such as a coronary artery 18 of the heart 16 or the carotid artery 14. In the example, this is achieved by moving the catheter head 58 up through the aorta 12.

When at the desired site, near infrared radiation (NIR) is generated by a laser source 100 and tuned over a scan band covering the spectral band of interest. It is coupled into the optical fiber of the catheter 56 to be transmitted to the catheter head 58.

In more detail, with reference to FIG. 1B, the tunable optical signal 102 for the optical fiber of the catheter 56 is directed by a fold mirror 62, for example, to exit from the catheter head 58 and impinge on the target area 22 of the artery wall 24. The catheter head 58 then collects reflected and scattered radiation from the target area 22.

Returning to FIG. 1A, the reflected light is transmitted back down the optical fibers of the catheter 56 to a splitter or circulator 54 or in separate optical fibers. This provides the returning radiation to a detector system 52, which can comprise one or multiple detectors.

The controller 60 monitors the response of the detector system 52, while controlling the tunable laser system 100 in order to probe the near infrared spectral response of the target area 22. The controller 60 with a power and wavelength detector subsystem 105 monitors the tunable laser system 100. This enables the controller 60 to track both the wavelength and power output of the tunable laser system 100.

Figure 2:
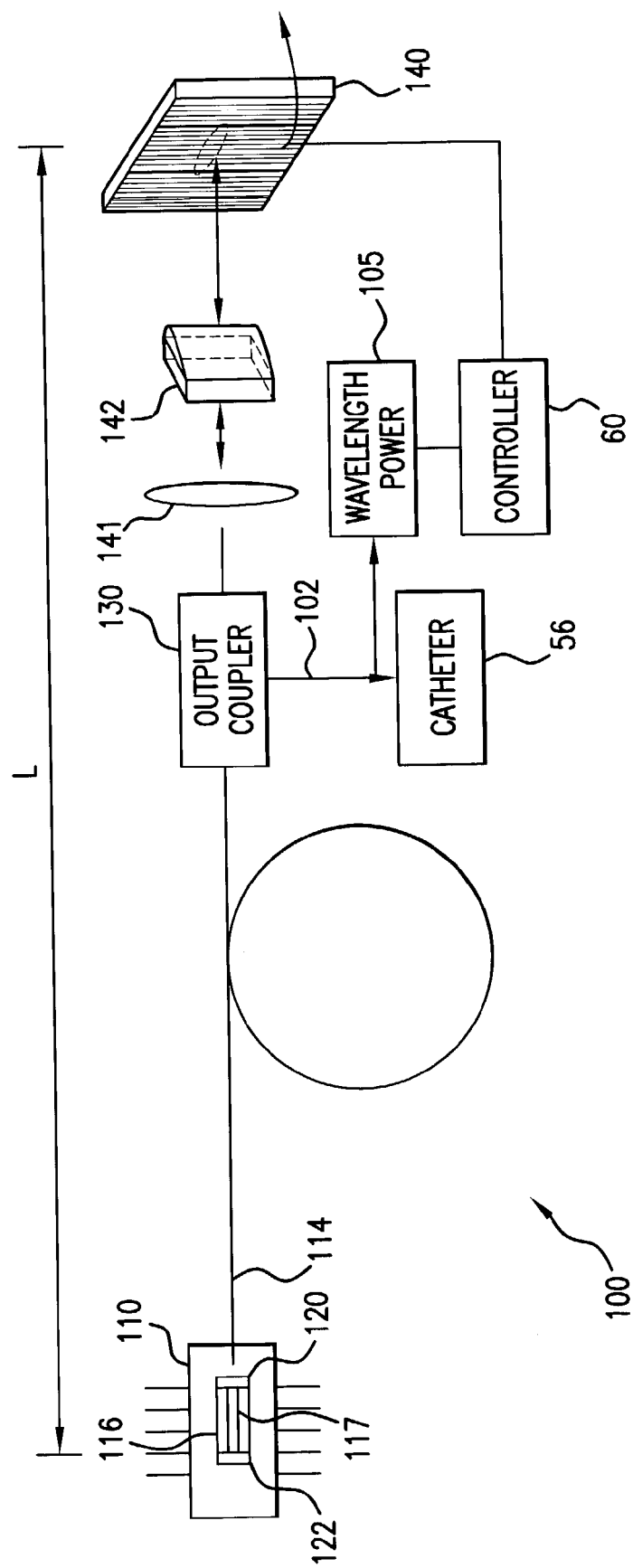
FIG. 2 is a schematic block diagram of a tunable laser source, according to the present invention.

FIG. 2 shows the general configuration of a tunable laser system 100, which has been constructed according to the principles of the present invention.

Specifically, it comprises at least one semiconductor optoelectronic module 110. In embodiments where wider tuning ranges or more power are required, multiple modules are used, such as two to eight or more, depending on the spectral range of interest and the total required power.

The module 110 comprises a semiconductor chip 116. In the preferred implementation, the chip 116 is a semiconductor optical amplifier chip, and specifically a reflective SOA. The chip's back facet has a highly reflective (HR) coating 122. The front facet has an anti-reflective (AR) coating 120. The chip's gain waveguide 117 acts as broadband optical energy source.

Light exiting from the front facet 120 of the chip 117 is coupled into a pigtail 114. Preferably, the pigtail 114 is single mode fiber that extends through a fiber feed-through in a hermetic package 112 of the module 110. This package 112 can be dual inline (DIP) or butterfly package depending on the implementation. In either case, the use of conventional hermetically packaged chips reduces the overall cost of the source 100.

In still other embodiments, standard, a double pigtailed SOA module can be used. In this case, back reflector feedback is preferably provided with a fiber Bragg gratings formed in one of the pigtails or by flat cleaving the pigtail and then HR coating the fiber facet.

The fiber pigtail 114 is preferably long to thereby create a long laser cavity. In the preferred embodiment, the optical length of the laser cavity is greater than 10 centimeters, and preferably it is longer than 50 centimeters. In some examples it has an optical length of greater than 1 meter.

This long cavity has the effect of creating a small cavity mode spacing of less than about 15 Gigahertz and even less than 1.5 Gigahertz. As a result, the laser cavity has greatly reduced ability to discriminate between longitudinal modes.

When the optical fiber is used as a waveguide for defining the cavity, the actual physical length of the cavity is less than the optical length since the index of refraction of the fiber 114 is greater than air. For example, typical single mode fiber has an index of refraction of about 1.4. Thus, if the optical length is 1 meter, then only about 70 centimeters of fiber is required.

An output coupler 130 receives the distal end of the pigtail 114 from the semiconductor modules 110. This output coupler 130 provides an output port for the laser cavity and specifically the output optical signal 102 that is coupled into the catheter 56. In the illustrated example, some of the output is used by the power and wavelength detector 105 to provide for feedback control of the tunable laser system 100 by the controller 60. In one implementation, the output coupler 130 is a three-port tap device.

Optical energy that is not provided as the output signal 102 is coupled to a frequency selective tunable element 140 via free space transmission using a collimator 142. In one example, the collimator 142 is a graded index or other type of lens. In the preferred embodiment, the collimator 142 is a cylindrical lens and is used in combination with a collimating focusing lens 141 to improve manufacturing tolerances.

The frequency selective tunable element 140 provides tunable feedback into the SOA chip 116 of the semiconductor module 110. In the present implementation, the frequency selected tunable element 140 is a diffraction grating. It is angle tuned under the control of the controller 60 to thereby modulate or change the feedback to the module 110 and thus control the wavelength of the output signal 102.

In a current implementation, the angle of the grating 140 is controlled using a resonant galvanometer. It preferably is tuned to scan the spectrum relatively quickly, in preferably less than 50 milliseconds (msec) to remove motion artifacts do to the beating of the heart. Presently, the spectrum is scanned in less than 10 msec or preferably 5 msec or less.

In other embodiments, other types of frequency selective tunable elements are used. For example, acousto-optic filters and Bragg gratings can be used in place of the diffraction grating.

The presently proposed configuration incorporates a 600 line/millimeter (mm) diffraction grating, which is 12×12×6 mm in size (Optometrics, LLC, Part No. 3-4669).

Figure 3:
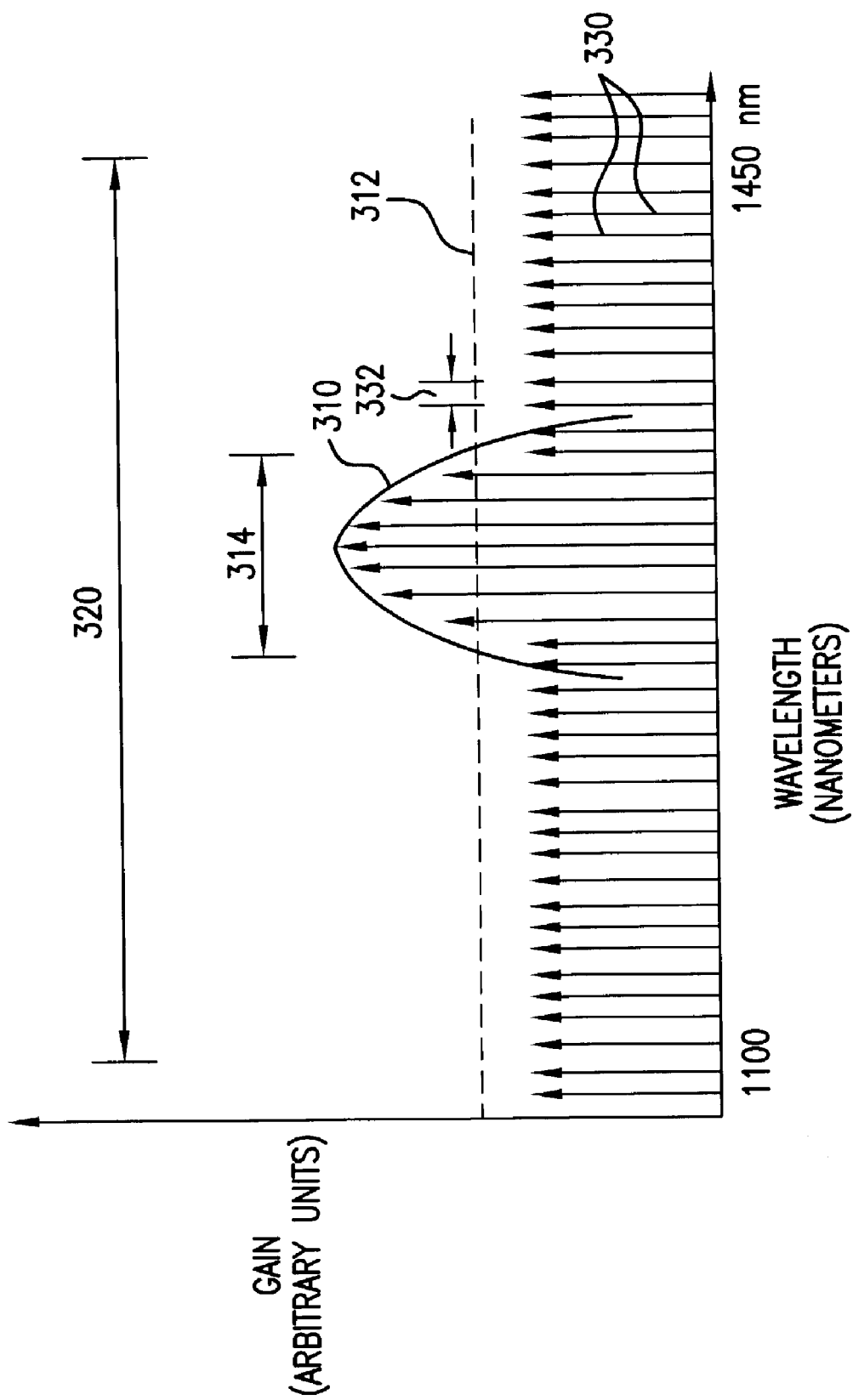
FIG. 3 is a plot of gain (arbitrary units) as a function of wavelength (nanometers) over the scan band for the inventive laser source.

FIG. 3 is a plot of gain as a function of wavelength over the scan band 320. Specifically, angle tuning the grating 140 has the effect of tuning a passband 310 over the scan band 320. The shape and more relevantly the spectral width of the passband 310 is a function of the resolution of the grating 140 in combination with the numerical aperture of the collimator 142 and any other aperturing between the fiber 114 and the grating 140. The passband characterizes the effective wavelength selectivity of the collimator/grating system.

In the present embodiment, the collimator/grating system is selected to have a relatively wide bandwidth. Specifically, the width of the passband that is above the lasing threshold 312, thus defining the gain bandwidth 314, is greater than 10 Gigahertz (GHz). Preferably, the gain bandwidth is greater than 50 GHz, and can be as large as 100 to 200 GHz, or more.

This wide band gain region results in a relatively wide band laser output signal 102. For some applications, this wide band, spectrally impure signal would be problematic. In the present application, the spectral features are also relatively wide and diffuse. Thus, the system still has the required spectral resolution for this application.

The wide gain bandwidth extends to cover multiple cavity modes 330. The modes will lase simultaneously if the gain medium is purely non-homogenously broadened. Thus, multiple cavity modes resonate since the cavity mode spacing 332 is smaller than the gain bandwidth 314. Specifically, the gain bandwidth is more than two times the cavity mode spacing. In the preferred embodiment, the combination of the cavity mode spacing, i.e., laser cavity length, and the gain bandwidth are such that 10 or more longitudinal modes will lase simultaneously.

Figure 4:
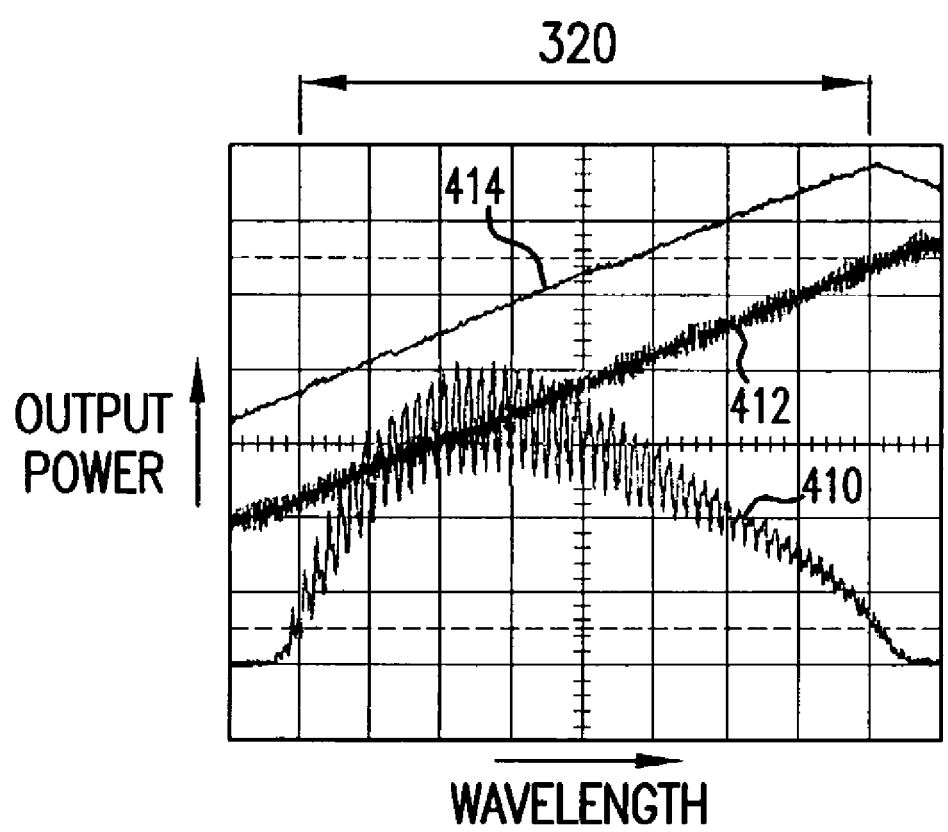
FIG. 4 is a plot of output power (arbitrary units) as a function of wavelength over the scan band for a conventional source and the inventive source.

FIG. 4 is a plot of output power and a function of wavelength across the scan band 320. Data Set 1 410 was taken from a conventional short cavity tunable laser. The oscillations in output power result from mode hopping. The gain bandwidth is thus on the order of the cavity mode spacing so that as the gain bandwidth is spectrally tuned over the cavity modes, different modes lase and see very different effective gain in the laser cavity. Data set 2 412 is derived from a longer cavity tunable laser in which the cavity is long enough so that more than a few modes are lasing continuously across the scan band. Mode hop induced power fluctuations are greatly reduced. Finally data set 3 was generated from a still longer cavity laser. Here the gain bandwidth encompasses ten or more modes. Mode-hoping induced power fluctuations are almost entirely removed.

While this invention has been particularly shown and described with references to preferred embodiments thereof, it will be understood by those skilled in the art that various changes in form and details may be made therein without departing from the scope of the invention encompassed by the appended claims.

What is claimed is:

1. A spectroscopic catheter system, comprising:
   a catheter for insertion into a patient to transmit light to the patient;
   a tunable laser source having a laser cavity including:
      a wavelength selector for scanning a passband over a scan band,
      a laser gain chip providing gain to modes of the laser cavity within a gain bandwidth provided by the passband; wherein the laser cavity is characterized by a cavity mode spacing that is two or more times smaller than the gain bandwidth and two or more longitudinal modes of the laser cavity are lasing at all times during the scanning of the passband over the scan band, and
      an output coupler for coupling laser light from laser cavity into the catheter; and
   at least one detector for detecting light returning from the patient to perform spectroscopic analysis.

2. A catheter system as claimed in claim 1, wherein the catheter is inserted into a lumen of the patient.

3. A catheter system as claimed in claim 1, wherein the catheter is inserted into a blood vessel of the patient.

4. A catheter system as claimed in claim 1, wherein the catheter is inserted into a blood vessel to a heart of the patient.

5. A catheter system as claimed in claim 1, wherein the wavelength selector comprises a diffraction grating.

6. A catheter system as claimed in claim 1, wherein the wavelength selector comprises a bulk diffraction grating.

7. A catheter system as claimed in claim 1, wherein the wavelength selector comprises a Bragg grating.

8. A catheter system as claimed in claim 1, wherein the laser cavity further comprises an optical fiber pigtail coupling the laser gain chip and the wavelength selector.

9. A catheter system as claimed in claim 1, wherein the laser gain chip comprises a semiconductor optical amplifier.

10. A catheter system as claimed in claim 1, wherein the laser gain chip comprises a reflective semiconductor optical amplifier.

11. A catheter system as claimed in claim 1, wherein an optical length of the laser cavity is greater than 10 centimeters.

12. A catheter system as claimed in claim 1, wherein an optical length of the laser cavity is greater than 50 centimeters.

13. A catheter system as claimed in claim 1, wherein an optical length of the laser cavity is greater than 1 meter.

14. A catheter system as claimed in claim 1, wherein the cavity mode spacing is less than 15 Gigahertz.

15. A catheter system as claimed in claim 1, wherein the cavity mode spacing is less than 1.5 Gigahertz.

16. A catheter system as claimed in claim 1, wherein the gain bandwidth is greater than 10 Gigahertz.

17. A catheter system as claimed in claim 1, wherein the gain bandwidth is greater than 50 Gigahertz.

18. A catheter system as claimed in claim 1, wherein the gain bandwidth is greater than 100 Gigahertz.

19. A catheter system as claimed in claim 1, further comprising at least two laser gain chips.

20. A catheter system as claimed in claim 1, wherein the laser gain chip is contained within a pigtailed hermetic package.

21. A method for providing tunable frequency light to a patient, the method comprising:
   inserting a catheter into a patient;
   generating light with a tunable laser comprising a laser gain chip that provides gain to laser cavity modes within a passband of a wavelength selector in a laser cavity of the tunable laser;
   tuning a frequency of the light across a scan band by scanning the passband of the wavelength selector over the scan band;
   selecting a length of the laser cavity of the tunable laser so that a cavity mode spacing of the laser cavity modes is two or more times smaller than a gain bandwidth of the laser cavity and two or more longitudinal modes of the laser cavity are lasing at all times during the step of tuning the frequency of the light across the scan band; and
   detecting light returning from the patient to determine a spectral response of tissue within the patient over the scan band.

22. A method as claimed in claim 21, wherein the step of selecting the length of the laser cavity comprises selecting the length so that ten or more longitudinal modes of the laser cavity are lasing at all times during the step of tuning the frequency of the light across the scan band.

* * * * *